US00PP27821P2

(12) United States Plant Patent
Dobres et al.

(10) Patent No.: US PP27,821 P2
(45) Date of Patent: Mar. 28, 2017

(54) ***PENSTEMON* PLANT NAMED 'NOVAPENAME'**

(50) Latin Name: *Penstemon hybrida*
Varietal Denomination: Novapename

(71) Applicant: CP DELAWARE, INC., Wilmington, DE (US)

(72) Inventors: Michael S. Dobres, San Javier (ES); Sloane M. Scheiber, Parkesburg, PA (US)

( * ) Notice: Subject to any disclaimer, the term of this patent is extended or adjusted under 35 U.S.C. 154(b) by 0 days.

(21) Appl. No.: 14/757,205

(22) Filed: Dec. 7, 2015

(51) Int. Cl.
*A01H 5/02* (2006.01)

(52) U.S. Cl.
USPC ..... Plt./465

(58) Field of Classification Search
USPC ..... Plt./465
See application file for complete search history.

*Primary Examiner* — Annette Para
(74) *Attorney, Agent, or Firm* — Buchanan Ingersoll & Rooney PC

(57) ABSTRACT

The new *Penstemon* plant was created by a controlled plant breeding program followed by selection, open pollination, and further selection. The growth habit is upright with strong basal branching and excellent vigor. Attractive large light-lavender flowers with a white throat on sturdy stems are formed. There is no vernalization requirement for flowering. An upright mounding growth habit is displayed. The plant readily roots from stem cuttings and is well suited for providing attractive ornamentation.

2 Drawing Sheets

Botanical/commercial classification: *Penstemon hybrida/ Penstemon* Plant.
Varietal denomination: cv. Novapename.

SUMMARY OF THE INVENTION

*Penstemon* plants, sometimes known as Beard Tongue, are herbaceous perennials which provide colorful flowers during the summer.

The new *Penstemon* plant of the present invention was created and discovered at West Grove, Pa., U.S.A. The female parent (e.g., seed parent) was an unnamed, non-patented breeder seedling resulting from the cross of *Penstemon mexicali* 'Pike's Peak Purple' (non-patented)×*Penstemon hartwegii* 'Giganteus' (non-patented). This breeder seedling, which served as the female parent, was selected from the progeny of the cross in view of its large blooms, increased branching, and extended length of bloom time. This female parent next underwent open pollination in a controlled plant nursery setting tended by man. Seed from this open pollination was collected during August 2011 and was grown in tissue culture before being acclimated to soil in October 2011. Seedlings were observed from the possible presence of promising novel photypes during the summer of 2012 when the plant of the present invention was selected on the basis of large colorful blossoms, well-branched growth habit, sturdy stems, and prolonged bloom time. Had this new plant not been selected and preserved it would have been lost to mankind.

The parentage of the new cultivar can be summarized as follows:

(*Penstemon mexicali* 'Pike's Peak Purple'×*Penstemon hartwegii* 'Giganteus')×Open Pollination.

It was found that the new *Penstemon* plant displays the following combination of characteristics:

(a) displays an upright growth habit with strong basal branching and excellent vigor, (b) is lacking a vernalization requirement for flowering,
(c) abundantly forms attractive large light-lavender flowers with a white throat on sturdy stems, and
(d) is well suited for providing attractive ornamentation.

During observations to date, the plant has been found to be hardy at U.S.D.A. Hardiness Zone No. 6. Trimming of the plant promotes further flowering.

The new cultivar well meets the needs of the horticultural industry and can be grown to advantage as a perennial garden plant to provide colorful ornamentation. The plant performs well when grown along borders or sidewalks as well as in containers.

Plants of the new cultivar can be readily distinguished from other *Penstemon* cultivars. More specifically, when compared to its 'Pike's Peak Purple' ancestor, the new cultivar displays lighter (more lilac) colored flowers that are considerably larger in size, and when compared to its 'Giganteus' ancestor displays large lighter lavender flowers unlike the bright red flowers of 'Giganteus'.

Also, when compared to the 'Blueberry Taffy' cultivar (U.S. Plant Pat. No. 22,568), the new cultivar displays larger light-lavender flowers with a white throat unlike the purple-blue flowers having a dark maroon ring at the base of the lobes and white throat of the 'Blueberry Taffy' cultivar. Also, the new cultivar displays considerably more branching than the 'Blueberry Taffy' cultivar The new cultivar readily roots from stem cuttings.

The rooting of vegetative cuttings has been used to asexually propagate the new cultivar at West Grove, Pa., U.S.A. It has been found that the characteristics of the new cultivar are stable and are reliably transmitted from one generation to another. Accordingly, the new cultivar can be asexually reproduced in a true-to-type manner.

The new cultivar of the present invention has been named 'Novapename', and will be marketed under the AMETHYST QUARTZ Trademark.

BRIEF DESCRIPTION OF THE PHOTOGRAPHS

The accompanying photographs illustrate typical flowering plants of the new cultivar in color as nearly true as it is reasonably possible make the same in color illustrations of this nature. The plants were approximately two years of age and were being grown outdoors on their own roots during June 2014 at West Grove, Pa., U.S.A. The plants had been asexually reproduced by the rooting of vegetative cuttings.

DETAILED BOTANICAL DESCRIPTION

Figure 1:
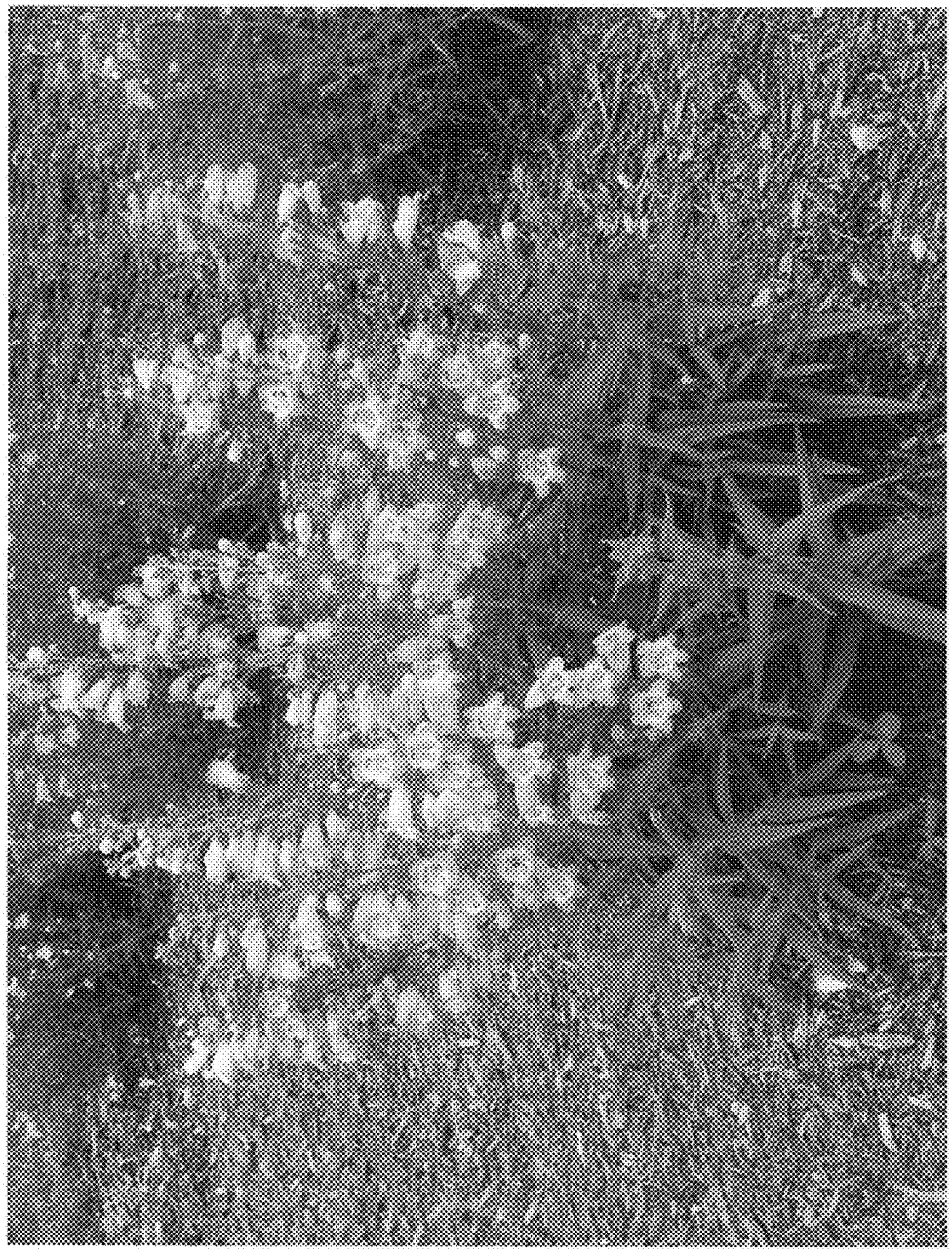
FIG. 1 illustrates the attractive upright growth habit of a flowering plant of the new cultivar.
Figure 2:
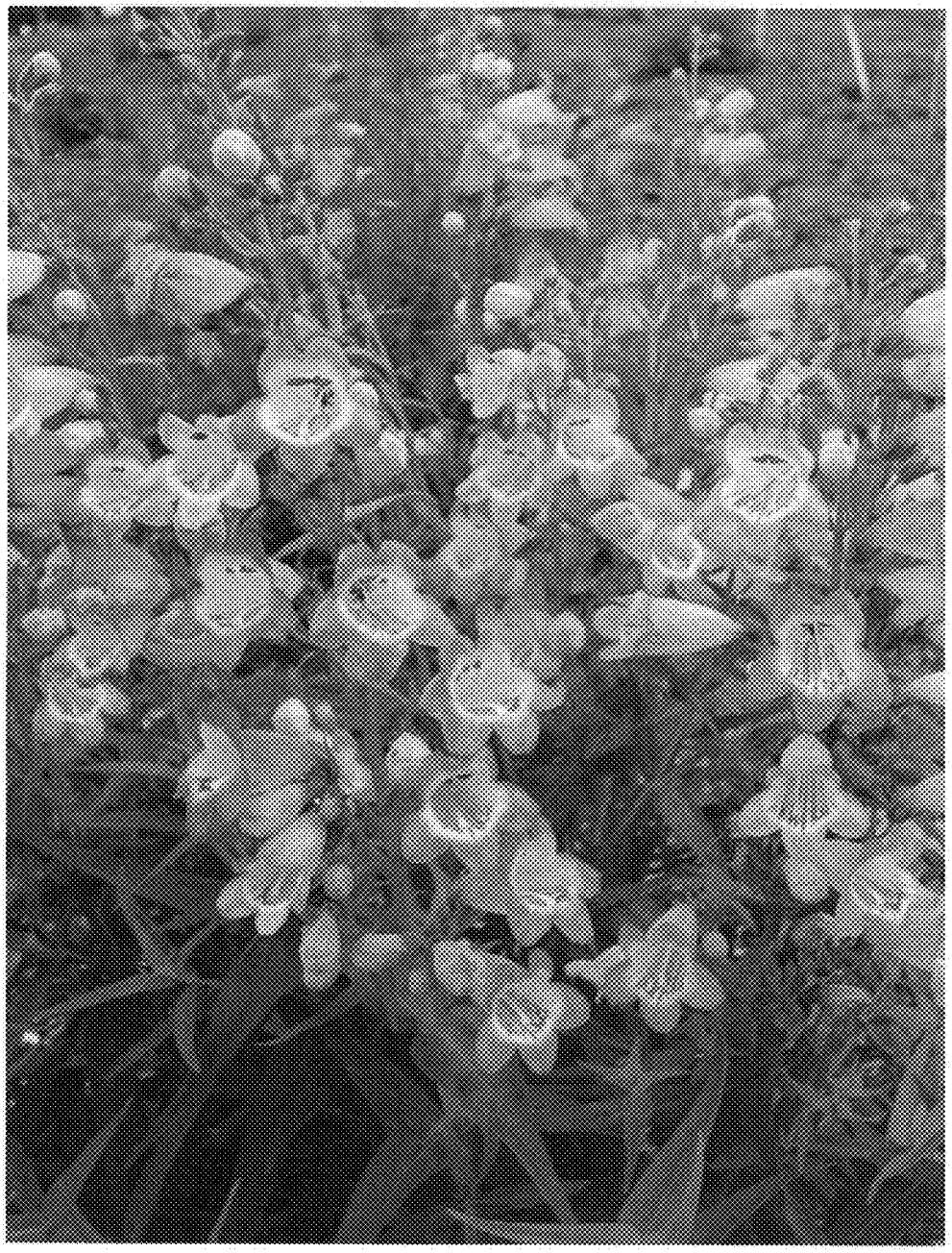
FIG. 2 illustrates a closer view of the blossoms in various stages of development and the foliage of the new cultivar.

The following is a detailed description while observing one-year-old plants of the new cultivar that were produced by the rooting of vegetative cuttings. Such plants were being grown in containers on their own roots at West Grove, Pa., U.S.A. The chart used in the identification of color is The R.H.S. Colour Chart (1995 Edition) of The Royal Horticultural Society, London, England. Common color terms are to be accorded their customary dictionary significance.

Botanical classification: *Penstemon*, cv. Novapename.

*Parents*.—Cross of 'Pike's Peak Purple'×'Giganteus', followed by selection, open pollination, and further selection.

*Plant type*.—Herbaceous perennial.

Plant:

*Growth habit*.—Upright with considerable branching.

*Height*.—Approximately 40 cm on average.

*Spread*.—Approximately 37.5 cm on average.

*Vigor*.—Excellent.

*Branching*.—Commonly approximately 14 stems on average arise at the base. During observations at West Grove, Pa., U.S.A., this compares to approximately 10 stems from the base for the 'Blueberry Taffy' cultivar.

*Stem length*.—Approximately 35 cm on average.

*Stem diameter*.—Approximately 1 cm at the base on average.

*Stem strength*.—Relatively strong.

*Stem color*.—Near Green Group 143C.

*Stem texture*.—Glabrous.

*Internode length*.—Commonly approximately 1.5 cm on average.

*Roots*.—Fibrous network.

Foliage:

*Arrangement*.—Opposite, simple, sessile.

*Shape*.—Lanceolate.

*Apex*.—Acuminate.

*Base*.—Truncate.

*Length*.—Commonly approximately 8.5 cm on average.

*Width*.—Commonly approximately 1 cm on average.

*Texture*.—Glabrous on the upper and under surfaces.

*Color*.—On the upper surface near Green Group 137A, and on the lower surface near Green Group 137B.

*Margins*.—Denticulate.

Inflorescence:

*Season*.—The natural flowering season when grown outside is primarily mid-June to frost in October.

*Type*.—Zygomorphic, perfect tubular, bi-labiate, terminal, many flowered, and dense thyrse.

*Buds*.—Ovoid, approximately 2.8 cm in length on average just before opening, approximately 1 cm in width on average, near Violet Group 87D on the upper surface and near Violet Group 84D on the lower surface.

*Quantity*.—Free-flowering, commonly with approximately 35 flowers on average developing per inflorescence.

*Inflorescence length*.—Approximately 22 cm on average.

*Inflorescence width*.—Approximately 7 cm on average.

*Fragrance*.—None detectable.

*Lastingness*.—Commonly 5 to 7 days on the plant depending on environmental conditions.

*Flower diameter*.—Approximately 3.8 cm on average.

*Flower length*.—Approximately 3 cm on average.

*Corolla tube*.—Approximately 3.8 cm in length and approximately 3 cm in width, funnel form in calyx with tube approximately 8 mm in length on average and approximately 5 mm in width on average, inflating for approximately 2 cm to a width of approximately 1.5 cm, and then flaring into 5 lobes, with two smaller upper lobes flaring back measuring approximately 8 mm×1 cm, the two larger lateral lobes flaring out measuring approximately 8 mm×8 mm, and the lower lobe flaring down measuring approximately 8 mm×6 mm. This compares to length of approximately 1.2 cm and a width of approximately 1.2 cm for the 'Pike's Peak Purple' cultivar.

*Corolla margins*.—Entire with obtuse tips.

*Corolla texture*.—Pubescent on the outside and glabrous on the inside.

*Corolla color*.—On the outside near Violet Group 84A at the bottom of the funnel and near Violet Group 85A, on the lobe backs, and on the inside of the outer lobes near Violet Group 87C with the 3 outer lobes having a ring of Red-Violet Group 81B which extends up their main veins in lines that tracks down the funnel, and the tube being near Purple-Violet Group 82A.

*Calyx*.—Five overlapping lobes extend from the base.

*Calyx lobe*.—Broadly ovate.

*Calyx size*.—Approximately 6 mm in length on average, and approximately 2 mm in width on average.

*Calyx apex*.—Acute.

*Calyx base*.—Cuneate.

*Calyx margin*.—Entire.

*Calyx texture*.—Glabrous on the inside and pubescent on the outside.

*Calyx color*.—Near Green Group 143A.

*Calyx shape*.—With five over-lapping lobes.

*Stamen number*.—Five.

*Anther opening*.—Tend to dehisce the full length across the connective and usually spread widely apart.

*Anther size*.—Approximately 1 mm×2 mm on average.

*Anther color*.—Near Violet Group 90B.

*Filaments*.—Commonly approximately 2.4 cm in length on average, and near White Group 155B in coloration.

*Pollen*.—Near White Group 155B in coloration.

*Pistil number*.—One.

*Pistil length*.—Approximately 2.5 cm on average.

*Style length*.—Approximately 1.9 cm on average.

*Style diameter*.—Commonly less than 1 mm.

*Style color*.—Commonly near Green-White Group 157B.

*Stigma color*.—Near Green-White Group 157B.
*Ovary length*.—Commonly approximately 6 mm on average.
*Ovary width*.—Commonly approximately 1.5 mm on average.
*Fruit type*.—Capsule.
*Fruit size*.—Commonly approximately 1 cm×4 mm on average.
*Fruit color*.—Near Brown Group 200A and 200B.
*Seed shape*.—Somewhat irregular.
*Seed size*.—Commonly approximately 1 mm in length and less than 1 mm in width.
*Seed color*.—Near Brown Group 200A.
*Peduncle length*.—Approximately 3 cm on average.
*Peduncle diameter*.—Approximately 1 mm on average.
*Peduncle texture*.—Pubescent.
*Peduncle color*.—Near Yellow-Green Group 144A.
*Pedicel length*.—Approximately 1.3 cm on average.
*Pedicel diameter*.—Approximately 1 mm on average.
*Pedicel texture*.—Pubescent.
*Pedicel strength*.—Relatively strong.
*Pedicel color*.—Near Yellow-Green Group 144A.

Disease resistance: The tolerance/susceptibility to diseases and pests common to *Penstemon* plants appears to be typical during observations to date. Plants of the 'Novapename' cultivar have not been observed under all possible environmental conditions to date. Accordingly, it is possible that the phenotypic expression may vary somewhat with changes in light intensity and duration, cultural practices, and other environmental conditions.

We claim:

1. A new and distinct *Penstemon* plant having the following combination of characteristics:

(a) displays an upright growth habit with strong basal branching and excellent vigor,
(b) is lacking a vernalization requirement for flowering,
(c) abundantly forms attractive large light-lavender flowers with a white throat on sturdy stems, and
(d) is well suited for providing attractive ornamentation;

substantially as illustrated and described.

* * * * *